(12) United States Patent
Ziegler et al.

(10) Patent No.: US 7,816,392 B2
(45) Date of Patent: Oct. 19, 2010

(54) CRYSTALLINE MODIFICATIONS TO PYRACLOSTROBIN

(75) Inventors: Hans Ziegler, Mutterstadt (DE); Winfried Mayer, Bubenheim (DE); Thomas Kröhl, Schriesheim (DE); Karl-Heinrich Schneider, Kleinkarlbach (DE); Gerhard Cox, Bad Dürkheim (DE); Peter Erk, Frankenthal (DE); Uwe Josef Vogelbacher, Ludwigshafen (DE); Rainer Noack, Großthiemig (DE); Roland Götz, Neulußheim (DE); Jörg Wuckelt, Schwarzheide (DE); Matthias Rauls, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 229 days.

(21) Appl. No.: 11/917,976

(22) PCT Filed: Jun. 19, 2006

(86) PCT No.: PCT/EP2006/005869

§ 371 (c)(1),
(2), (4) Date: Dec. 18, 2007

(87) PCT Pub. No.: WO2006/136357

PCT Pub. Date: Dec. 28, 2006

(65) Prior Publication Data

US 2008/0234350 A1    Sep. 25, 2008

(30) Foreign Application Priority Data

Jun. 20, 2005    (DE)    ........................ 10 2005 028 493

(51) Int. Cl.
*A01N 43/56*    (2006.01)
*A01P 3/00*    (2006.01)
*C07D 231/18*    (2006.01)

(52) U.S. Cl. .................................. 514/407; 548/370.1

(58) Field of Classification Search ................ 514/407; 548/370.1

See application file for complete search history.

(56) References Cited

U.S. PATENT DOCUMENTS

| 6,054,592 A | 4/2000 | Müller et al. |
| 2003/0199394 A1* | 10/2003 | Finch et al. .................. 504/282 |

FOREIGN PATENT DOCUMENTS

| WO | WO 96/01256 | 1/1996 |
| WO | WO 03/082013 | 10/2003 |

OTHER PUBLICATIONS

Herms, S. et al., "Pyraclostrobin—More than just a fungicide", Phytomedzin, 2002, p. 17, vol. 32.
English Translation of "International Preliminary Report on Patentability," PCT/EP2006/005869, issued Jan. 24, 2008.

* cited by examiner

*Primary Examiner*—Yong Chu
(74) *Attorney, Agent, or Firm*—Brinks Hofer Gilson & Lione (57) ABSTRACT

The present invention relates to novel crystalline modifications of pyraclostrobin, to processes for their preparation and to the use of the novel modifications for preparing crop protection compositions.

17 Claims, 3 Drawing Sheets

Figure 1: Powder diffractogram of pyraclostrobin modification IV

Figure 2: Powder diffractogram of pyraclostrobin modification II

Figure 3: Powder diffractogram of pyraclostrobin modification I

Figure 4: Powder diffractogram of pyraclostrobin modification III

CRYSTALLINE MODIFICATIONS TO PYRACLOSTROBIN

The present invention relates to novel crystalline modifications of pyraclostrobin, to processes for their preparation and to the use of the novel modifications for preparing crop protection compositions.

Pyraclostrobin (methyl N-[[[1-(4-chlorophenyl)pyrazol-3-yl]oxy]-o-tolyl]-N-methoxy-carbamate) is an active compound for controlling phytopathogenic fungi (see, for example, WO 96/01256 and Herms, S., Seehaus, K., Koehle, H., and Conrath, U. (2002) Pyraclostrobin—"More than just a Fungicide" Phytomedizin 32: 17). Commercially available pyraclostrobin is an amorphous substance of low melting point. Owing to this property, commercially available pyraclostrobin is not suitable for preparing aqueous suspension concentrates (SC) in a conventional manner, since the grinding apparatus will get stuck during grinding as a result of the tackiness of the substance. For this reason, commercial preparation by conventional means of biologically and economically interesting mixed products of pyraclostrobin with other crop protection agents in the form of suspension concentrates has hitherto not been possible.

For this reason, pyraclostrobin is frequently formulated in the form of solvent-comprising emulsion concentrates or suspoemulsion concentrates or in the form of water-dispersible granules. However, emulsion concentrates and suspoemulsion concentrates comprise relatively large amounts of organic, water-immiscible solvents, for example aromatic hydrocarbons, so that these formulations are problematic both for environmental protection reasons and for work hygiene reasons. Moreover, in the case of pyraclostrobin suspoemulsion concentrates, active compound particles may separate off during storage under certain conditions.

WO 03/082013 proposes the preparation of active compound particles by applying a pyraclostrobin melt to a carrier material. Using the resulting adsorbates, suspension concentrates, into which mixing partners may also be introduced, can be prepared by customary processes. However, in these suspension concentrates, there may be an irreversible particle size increase of the dispersed active compound particles after some time, in particular on storage at elevated temperature. This has a pronounced negative effect on the quality of the product. Moreover, the process is relatively complicated since it requires additional materials and process steps.

Accordingly, it is an object of the present invention to provide pyraclostrobin in a form which permits the preparation of suspension concentrates having improved stability.

This object is achieved by the crystalline modifications II and IV, described in more detail below, of pyraclostrobin.

Thus, the invention relates firstly to a crystalline modification IV of pyraclostrobin which, in an X-ray powder diffractogram at 25° C., shows at least three, in particular at least 4 and preferably all of the following reflexes:

$$d=6.02\pm0.01\ \text{Å}$$

$$d=4.78\pm0.01\ \text{Å}$$

$$d=4.01\pm0.01\ \text{Å}$$

$$d=3.55\pm0.01\ \text{Å}$$

$$d=3.01\pm0.01\ \text{Å}.$$

Crystalline pyraclostrobin of modification IV has typically a melting point in the range from 62 to 72° C., in particular in the range from 64 to 68° C. and especially in the range from 65 to 67° C. The heat of fusion, i.e. the amount of energy required for melting the crystalline modification IV, is about 72 to 78 J/g and in particular about 74±1 J/g. The melting points and heats of fusion indicated here refer to values determined by differential calorimetry (Differential Scanning Calorimetry: DSC, crucible material aluminum, heating rate 5 K/min).

Studies of single crystals of modification IV show that the basic crystal structure is monoclinic and has the space group P2(1)/c. The characteristic data of the crystal structure of modification IV are shown in Table 1:

TABLE 1

Crystallographic data of modification IV

| Parameter | Modification IV |
|---|---|
| Class | Monoclinic |
| Space group | P2(1)/c |
| a | 998.5(3) pm |
| b | 4780.4(10) pm |
| c | 788.6(2) pm |
| α | 90° |
| β | 105.357(6)° |
| γ | 90° |
| Volume | 3.6301(16) $nm^3$ |
| Z | 8 |
| Density (calculated) | 1.419 $g/cm^3$ |
| R1, wR2 | 0.0651, 0.1574 | a, b, c = Length of the edges of the unit cell
α, β, γ = Angles of the unit cell
Z = Number of molecules in the unit cell The crystalline modification IV of pyraclostrobin can be prepared using a process (hereinbelow also referred to as process IVa), which comprises the following steps:

i) dissolving a pyraclostrobin form different from modification IV in an organic solvent or solvent mixture, where the organic solvent or solvent mixture comprises at least 70% by volume of at least one fully water-miscible organic solvent L1 and if appropriate up to 30% by volume of water; and ii) effecting crystallization of pyraclostrobin over a period of at least 10 h, in particular at least 15 h and especially at least 20 h and/or in the presence of seed crystals of modification IV.

Suitable pyraclostrobin forms different from modification IV are, for example, a solid or liquid pyraclostrobin melt, amorphous pyraclostrobin or a pyraclostrobin of modifications I, II or III, or mixtures thereof. In a preferred embodiment, a melt of the pyraclostrobin is dissolved in one of the abovementioned organic solvents or solvent mixtures. The pyraclostrobin used preferably has a purity of at least 90%, in particular at least 95% and especially at least 98%.

Solvent L1 may be a pure solvent L1 or a mixture of different solvents L1. According to the invention, solvent L1 is fully miscible with water. This is to be understood as meaning that, at 25° C. (and 1023 mbar), the solvent is fully miscible with water, i.e. does not have a miscibility gap with water at the temperature mentioned. Preferred are solvents L1 which are fully miscible with water at 1023 mbar over a relatively large temperature range, in particular the entire temperature range relevant for the crystallization, i.e. the range from 0 to 80° C., but at least the temperature range from 10 to 60° C., i.e. do not have a miscibility gap with water in these temperature ranges. The person skilled in the art is familiar with suitable solvents, which can be found in the specialist literature and appropriate reference books, such as the Handbook of Chemistry and Physics, CRC Press, Ullmanns Encyclopedia of Industrial Chemistry, 5th ed. on CD ROM, Wiley-VCH, 1997 (chapter Solvents) and Industrial Solvents Handbook, 2nd ed. Marcel Dekker 2003. Preference is furthermore given to solvents L1 whose boiling point at atmospheric pressure is in the range from 50 to 100° C.

Preferred solvents L1 are $C_1$-$C_4$-alkanols, such as methanol, ethanol, n-propanol, isopropanol, n-butanol, isobutanol, 2-butanol and tert-butanol, and also acetone and butanone, and mixtures thereof. Particularly preferred solvents L1 are methanol, ethanol, n-propanol and isopropanol and mixtures thereof, and especially methanol and ethanol and mixtures thereof, furthermore acetone and butanone.

In addition to the solvent L1, the solvent or solvent mixture used for dissolving the pyraclostrobin may comprise further solvents different from L1. Typical further organic solvents which can be used in a mixture with the solvent L1 are, for example:

- alkanols having at least 5 carbon atoms, in particular 5 to 12 carbon atoms, such as amyl alcohol, isoamyl alcohol, hexanols, such as n-hexanol, 2-ethyl-1-butanol, 4-methyl-2-pentanol, 2-ethylhexanol, isononanol, n-nonanol, technical-grade mixtures of isomeric nonyl alcohols, 2-propylheptanol, isotridecanol, technical-grade mixtures of isomeric isotridecanols, and the like;
- cycloalkanols having at least 5 carbon atoms, in particular 5 to 12 carbon atoms, such as cyclopentanol, cyclohexanol, cycloheptanol, 2-, 3- and 4-methylcyclohexanol, 3,3,5-trimethylcyclohexanol and the like;
- aliphatic and cycloaliphatic ketones having 3 to 12 carbon atoms, such as acetone, methyl ethyl ketone, diethyl ketone, methyl propyl ketone, methyl butyl ketone, methyl isobutyl ketone, cyclohexanone, methylcyclohexanone, dimethylcyclohexanone, 3,3,5-trimethylcyclohexanone, isophorone and the like;
- $C_1$-$C_8$-alkyl esters and $C_5$-$C_{10}$-cycloalkyl esters of aliphatic $C_1$-$C_4$-carboxylic acids, in particular of acetic acid, such as methyl acetate, ethyl acetate, n-propyl acetate, n-butyl acetate, isobutyl acetate, sec-butyl acetate, n-amyl acetate, isoamyl acetate, hexyl acetate, 2-ethylhexyl acetate, octyl acetate, cyclohexyl acetate, 2-butoxyethyl acetate, and the corresponding propionates and butyrates;
- diols having 2 to 8 carbon atoms, in particular glycol, propanediol, butanediol, hexanediol, 2-ethylhexane-1, 3-diol and 2,4-diethyloctane-1,5-diol;
- N-di-$C_1$-$C_4$-alkylamides of aliphatic carboxylic acids and $C_1$-$C_4$-alkyllactams, such as N,N-dimethylformamide, N,N-dimethylacetamide, N-methylpyrrolidone, N-ethylpyrrolidone and the like; and also
- aromatic hydrocarbons, in particular mono- or di-$C_1$-$C_4$-alkyl-substituted benzene, especially toluene and xylenes.

The proportion of the solvents different from L1 and in particular from $C_1$-$C_4$-alkanols will preferably not exceed 30% by volume, in particular 20% by volume, particularly preferably 10% by volume and especially 5% by volume, based on the total amount of the solvent used for dissolving pyraclostrobin.

In process IVa, for dissolving the pyraclostrobin in step i), use is made in particular of methanol, ethanol or a mixture of organic solvents which comprises at least 70% by volume, in particular at least 80% by volume and especially at least 90% by volume of at least one $C_1$-$C_4$-alkanol selected from the group consisting of methanol and ethanol.

In addition to the organic solvents mentioned above, the organic solvent used for dissolving the pyraclostrobin may comprise up to 30% by volume, preferably not more than 20% by volume, in particular not more than 10% by volume or not more than 5% by volume, for example from 0.1 to 20% by volume or from 0.1 to 10% by volume and especially from 0.2 to 5% by volume, of water.

For dissolving the pyraclostrobin form different from modification IV, the pyraclostrobin will usually be incorporated into the solvent as a finely divided solid or as a melt with mixing at a temperature where the solvent or solvent mixture is capable of completely dissolving the pyraclostrobin. In a preferred embodiment of the invention, the pyraclostrobin is dissolved at elevated temperature, in particular at at least 50° C., especially at at least 55° C., where the temperature used for dissolution will, of course, not exceed the boiling point of the solvent. Frequently, temperatures in the range from 50 to 100° C., in particular in the range from 55 to 90° C. and particularly preferably in the range from 60 to 80° C. are used for the dissolution. The amount of pyraclostrobin dissolved in solvent L1 depends, of course, on the nature of the solvent L1 and on the dissolution temperature and is frequently in the range from 100 to 800 g/l, in particular in the range from 120 to 700 g/l. The person skilled in the art will be able to determine suitable conditions by standard experiments.

The pyraclostrobin is then crystallized. Crystallization can be achieved in a customary manner, for example by cooling the solution obtained in step i), by adding a solvent which reduces the solubility, in particular by adding water, or by concentrating the solution, or by a combination of the measures mentioned above.

To achieve a conversion into modification IV which is as complete as possible, the crystallization is carried out over a period (duration of crystallization) of at least 15 h, in particular at least 20 h, and/or in the presence of seed crystals of modification IV.

Duration of crystallization is understood by the person skilled in the art as meaning the period of time between the beginning of the measure which initiates crystallization and the isolation of the pyraclostrobin by separating the crystalline material from the mother liquor.

In general, the crystallization is allowed to proceed to a point where at least 80%, preferably at least 90%, in particular at least 95% by weight, for example from 95 to 99.8% by weight, of the pyraclostrobin employed has crystallized out.

If seed crystals are added during the crystallization, their amount is typically from 0.001 to 10% by weight, frequently from 0.005 to 5% by weight, in particular from 0.01 to 1% by weight and especially from 0.05 to 0.5% by weight, based on the pyraclostrobin dissolved. In this case, the duration of crystallization is typically at least 2 h, in particular at least 4 h and especially at least 5 h; however, the crystallization can also be carried out over a relatively long period of time of up to a number of days, for example 2 to 3 days. However, frequently the duration of crystallization will not exceed 24 h and especially 14 h. Accordingly, the crystallization is generally carried out over a period of from 2 h to 2 d, frequently from 4 to 24 h and in particular from 5 h to 14 h.

If the crystallization of modification IV is carried out in the absence of seed crystals, the duration of crystallization is generally at least 10 h, in particular at least 15 h, especially at least 20 h, and will generally not exceed 21 d, frequently 7 d.

In a preferred embodiment of the invention, the pyraclostrobin is dissolved at elevated temperature, preferably at at least 50° C., for example at from 50 to 100° C., preferably from 55 to 90° C. and particularly preferably in the range from 60 to 80° C., and crystallization of the pyraclostrobin is then effected by cooling the solution. Preferably, the pyraclostrobin solution is cooled by at least 20 K, in particular by 30 to 50 K, to initiate crystallization. Cooling may be carried out in a controlled manner, i.e. the solution is cooled using a low cooling rate of generally not more than 20 K/h, for example from 0.5 to 20 K/h and frequently from 1 to 15 K/h. Controlled cooling is advantageously carried out when the crystallization begins. However, it is also possible to cool more rapidly, in which case the crystals will be agitated over a relatively long period of time in the mother liquor, i.e. until the desired duration of crystallization is reached, prior to isolation.

If the crystallization is carried out in the presence of seed crystals of modification IV, these are preferably added only at a temperature where the saturation concentration of pyraclostrobin in the solvent in question has been reached, i.e. at or below the temperature where the dissolved amount of pyraclostrobin forms a saturated solution in the solvent in question. The temperature dependence of the saturation concentration in a solvent can be determined in standard experiments by the person skilled in the art. Frequently, the seed crystals are added when the temperature of the solution is not more than 50° C. and in particular not more than 40° C. After addition of the seed crystals, the solution is preferably allowed to cool to temperatures below 30° C., in particular of 25° C. or below, for example to temperatures in the range from 5° C. to 25° C., before the resulting crystalline material is separated from the mother liquor to isolate the modification IV of pyraclostrobin. Cooling in the presence of seed crystals can be carried out in a controlled manner using a cooling rate of generally not more than 30 K/h, for example from 1 to 30 K/h, frequently from 2 to 20 K/h and in particular from 3 to 15 K/h, or in an uncontrolled manner.

It has been found to be advantageous to agitate the crystalline material for an extra period of time at temperatures below the crystallization temperature, for example in the range from 10 to 35° C., in the mother liquor, for example from 1 h to 124 h or from 2 h to 96 h, to ensure complete conversion into modification IV. In this case, the total duration from beginning of the cooling to the isolation of the crystals by removal of the mother liquor is then in the ranges mentioned above.

In a particularly preferred embodiment of process IVa, the pyraclostrobin is initially dissolved in the solvent mentioned above, in particular in a solvent or solvent mixture which comprises at least 70% by volume, frequently at least 80% by volume, in particular at least 90 and especially at least 95% by volume of at least one $C_1$-$C_4$-alkanol selected from the group consisting of methanol and ethanol, at elevated temperature in the temperature ranges mentioned above, in particular at from >50 to 90° C. and especially in the range from 60 to 80° C., followed by cooling of the solution, preferably to a temperature in the range from 20 to 50° C. and in particular to from 30 to 40° C. Cooling is preferably carried out over a relatively long period of time, for example over a period of from 2 to 24 h, frequently from 4 to 20 h, using a cooling rate of, preferably, from 1 K/h to 20 K/h and in particular from 3 to 15 K/h. Seed crystals of modification IV are then added to the solution cooled in this manner. The solution is then cooled further by at least 5 K and in particular by at least 10 K, for example by 5 to 40 K and in particular by 10 to 30 K, for example to temperatures of from 0 to 40° C. and in particular to from 5 to 30° C. The second cooling is preferably carried out over a period of from 1 to 10 h, in particular from 2 to 6 h, advantageously using a cooling rate of from 2 to 20 K/h and in particular from 3 to 15 K/h. During this cooling, the pyraclostrobin crystallizes.

Alternatively, the crystallization can also be effected by addition of water, for example from 5 to 60% by volume, in particular from 20 to 55% by volume and especially from 30 to 50% by volume, based on the volume of the solvent or solvent mixture used for dissolving the pyraclostrobin. The addition of water is preferably carried out over a relatively long period of time, for example over a period of from 30 min to 10 h, in particular over a period of from 1 h to 8 h. In particular, the addition of water and the addition of seed crystals will be combined. The water may be added in the form of pure water or in the form of a mixture of water with one of the solvents L1 mentioned above or in a mixture with an organic solvent mixture which comprises predominantly L1, i.e. at least 70% by volume of L1, based on the organic solvent, in particular in a mixture with the solvent used for the dissolution. In the latter case, the proportion of organic solvent in the added water-containing mixture is typically in the range from 10 to 70% by volume, in particular from 20 to 60% by volume and especially from 40 to 50% by volume.

In a particularly advantageous manner, the pyraclostrobin is crystallized by a combination of cooling and addition of water. In particular, a crystallization of the pyraclostrobin is initially effected by cooling, preferably with addition of seed crystals, in the manner described above, and the crystallization of the pyraclostrobin is then brought to completion by addition of water in the amounts mentioned above. In particular, the water will be added at a temperature at which part of the pyraclostrobin present in the solution, for example from 5 to 90% by weight and in particular from 10 to 80% by weight, has already crystallized. The water is added in particular at temperatures in the range from 5 to 40° C. and especially in the range from 10 to 30° C. In particular, water will be added such that the amount of water, based on the total amount of solvent+water, is in the range from 20 to 55% by volume and especially from 30 to 50% by volume. Water is added, in particular, over a period of from 30 min to 8 h and particularly preferably over a period of from 1 h to 5 h.

The modification IV is isolated using customary techniques for separating solid components from liquids, for example by filtration, centrifugation or decanting. In general, the isolated solid will be washed, for example with the solvent used for the crystallization, with water or with a mixture of the organic solvent used for the crystallization with water. The washing can be carried out in one or more steps, and frequently, the last washing step is carried out with water. The washing is typically carried out at temperatures of below 30° C., frequently below 25° C. and in particular below 20° C., to keep the loss of the product of value as low as possible. The resulting modification IV can then be dried and subjected to further processing. However, frequently, the moist active compound obtained after washing, in particular a water-moist active compound, will be subjected to further processing.

In another process for preparing the crystalline modification IV of pyraclostrobin (hereinbelow also referred to as process IVb), the following steps are carried out:
  i) preparing a suspension of a pyraclostrobin form different from modification IV in an organic solvent (solvent L2);
  ii) if appropriate, adding seed crystals of modification IV to the suspension;
  iii) agitating the suspension until at least 90% of the pyraclostrobin is present in the form of modification IV.

In process IVb, in principle, it is possible to use all forms of pyraclostrobin different from modification IV mentioned for process IVa. With respect to purity, what was said for process IVa applies.

The solvent L2 is typically an organic solvent or solvent mixture capable of dissolving the pyraclostrobin at least partially, if appropriate at elevated temperature. It is in particular an organic solvent or solvent mixture in which, at a temperature of 40° C., pyraclostrobin has a solubility of at least 100 g/l and advantageously of not more than 800 g/l, in particular of not more than 700 g/l.

Examples of suitable solvents L2 comprise the $C_1$-$C_4$-alkanols, alkanols having 5 to 12 carbon atoms, cycloalkanols having 5 to 12 carbon atoms, aliphatic and cycloaliphatic ketones having 3 to 12 carbon atoms, $C_1$-$C_8$-alkyl esters and $C_5$-$C_{10}$-cycloalkyl esters of aliphatic $C_1$-$C_4$-carboxylic acids, in particular of acetic acid, diols having 2 to 8 carbon atoms, N-di-$C_1$-$C_4$-alkylamides of aliphatic carboxylic acids and $C_1$-$C_4$-alkyllactams and also aromatic hydrocarbons, in particular mono- or di-$C_1$-$C_4$-alkyl-substituted benzene, mentioned among the solvents L1, and mixtures of these solvents.

Advantageously, the organic solvent L2 used for suspending the pyraclostrobin comprises at least 50% by volume, in particular at least 60% by volume, particularly preferably at least 70% by volume, very particularly preferably at least 80% by volume and especially at least 90% by volume of at least one $C_1$-$C_4$-alkanol, particularly preferably methanol, ethanol, n-propanol and isopropanol. Correspondingly, the proportion of solvents different from $C_1$-$C_4$-alkanols will preferably not exceed 50% by volume, in particular 40% by volume, particularly preferably 30% by volume, very particularly preferably 20% by volume, and especially 10% by volume.

In process IVb, for suspending the pyraclostrobin in step i), use is made, in particular, of isopropanol, ethanol or a mixture of organic solvents comprising at least 70% by volume, in particular at least 80% by volume, particularly preferably at least 90% by volume, of isopropanol and/or ethanol.

In addition to the organic solvents mentioned above, the organic solvent L2 may comprise small amounts, preferably not more than 25% by volume, in particular not more than 10% by volume and particularly preferably not more than 5% by volume, of water.

To prepare the suspension, solid or molten pyraclostrobin can be suspended in the solvent L2 in a manner known per se, where the temperature of the solvent L2 and the amount of pyraclostrobin are chosen such that the pyraclostrobin is not fully dissolved. A person skilled in the art is able to determine these parameters by standard experiments. Typically, a temperature in the range of from 20 to 40° C. will be chosen. The amount of pyraclostrobin suspended in the solvent L2 is frequently in the range from 100 to 800 g/l, in particular in the range from 120 to 700 g/l. Typically, shear forces are used for suspending the solid or molten pyraclostrobin, for example by stirring the suspension using a suitable stirrer. Suitable stirrer types are familiar to the person skilled in the art, for example from M. Zlokarnik, Stirring, in Ullmann's Encyclopedia of Industrial Chemistry, 5th ed. on CD-ROM, Wiley-VCH 1997.

In a preferred embodiment of the invention, the suspension is prepared by initially completely or virtually completely dissolving pyraclostrobin in the solvent L2, in an advantageous manner by using elevated temperature, in particular temperatures in the range from 40 to 80° C., and then carrying out a partial crystallization of the pyraclostrobin, typically by concentration and/or by lowering the temperature, typically by at least 10 K, in particular by at least 20 K, for example by from 20 to 50 K.

The suspension obtained in this manner is then, if appropriate with addition of seed crystals of modification IV, agitated until the conversion into the modification is complete, i.e. the content of modification IV in the suspended solid is at least 90% by weight. The time required to achieve this can be determined in a standard memo by the person skilled in the art by taking samples and analyzing the material by X-ray powder diffractometry (XRD) or DSC.

If the conversion is carried out with addition of seed crystals, the suspension will typically be agitated for 12 to 48 h, in particular for 14 to 36 h, to achieve the desired conversion, longer periods not being disadvantageous. With respect to the amount of seed crystals, what was said above for process IVa applies analogously. The seed crystals are typically added to the suspension at temperatures in the range from 20 to 40° C. If the process is carried out without seed crystals, the suspension will preferably be agitated for at least 24 h, in particular at least 48 h and particularly preferably at least 72 h, before the crystalline material is separated from the mother liquor.

The temperature of the suspension is advantageously in the range from 20 to 40° C. Agitation is typically by stirring.

The isolation of modification IV from the suspension and further processing can be carried out in the manner described for process IVa.

The processes IVa and IVb according to the invention afford the crystalline modification IV with a pyraclostrobin content of at least 98% by weight, in particular at least 99% by weight. The amount of modification IV, based on the total amount of pyraclostrobin, is typically at least 90%, frequently at least 95% and in particular at least 98%. In the context of the studies of the crystalline modification IV, three further crystalline modifications of pyraclostrobin (modifications I, II and III) were found. Modifications I, II and III of pyraclostrobin are thermodynamically more stable than amorphous pyraclostrobin, but only metastable with respect to modification IV, and under certain conditions they are converted into modification IV. With respect to stability, the following applies: stability (modification I)<stability (modification II)<stability (modification III)<stability (modification IV). Modifications I, II, III and IV form a monotropic phase system (enthalpy of fusion).

In an X-ray powder diffractogram at 25° C., the crystalline modification I of pyraclostrobin shows at least four, in particular at least five, frequently at least six and especially all of the following reflexes:

$d=6.57\pm0.01$ Å

$d=5.80\pm0.01$ Å

$d=4.78\pm0.01$ Å

$d=4.22\pm0.01$ Å

$d=3.96\pm0.01$ Å

$d=3.52\pm0.01$ Å

$d=3.42\pm0.01$ Å

$d=3.34\pm0.01$ Å.

Crystalline pyraclostrobin of modification I typically has a melting point in the range from 55 to 56° C. The heat of fusion, i.e. the amount of energy required for melting the crystalline modification I, is about 63 to 66 J/g and in particular about 65±1 J/g.

Modification I of pyraclostrobin is typically obtained on cooling of a pyraclostrobin melt when the purity of the pyraclostrobin used for preparing the melt is at least 95%. By tempering the material at temperatures in the range from 40 to 50° C., crystallization of modification I can be accelerated. However, tempering will preferably be carried out for not more than 14 days, since otherwise there will be conversion into the more stable modifications II and III.

In an X-ray powder diffractogram at 25° C., the crystalline modification II of pyraclostrobin shows at least four, typically at least five, frequently at least six, in particular at least 7 and especially all of the following reflexes:

$d=5.93\pm0.01$ Å

$d=5.82\pm0.01$ Å

$d=4.89\pm0.01$ Å

$d=4.78\pm0.01$ Å

$d=4.71\pm0.01$ Å

$d=3.97\pm0.01$ Å

$d=3.89\pm0.01$ Å

$d=3.77\pm0.01$ Å

$d=3.75\pm0.01$ Å

$d=3.57\pm0.01$ Å

$d=3.43\pm0.01$ Å.

Crystalline pyraclostrobin of modification II typically has a melting point in the range from 57 to 58° C. The heat of fusion, i.e. the amount of energy required for melting the crystalline modification II, is about 67 to 70 J/g and in particular about 69±1 J/g.

Studies with single crystals of modification II show that the basic crystal structure is triclinic and has the space group P-1. The characteristic data of the crystal structure of modification II are listed in Table 2:

TABLE 2

| Crystallographic data of modification II | |
|---|---|
| Parameter | Modification IV |
| Class | Triclinic |
| Space group | P-1 |
| a | 789.69(16) pm |
| b | 1012.40(14) pm |
| c | 1228.9(2) pm |
| α | 96.733(10)° |
| β | 99.833(14)° |
| γ | 105.405(12)° |
| Volume | 0.9194(3) nm$^3$ |
| Z | 2 |
| Density (calculated) | 1.401 mg/m$^3$ |
| R1, wR2 | 0.0606, 0.1414 | a, b, c = Length of the edges of the unit cell
α, β, γ = Angles of the unit cell
Z = Number of molecules in the unit cell Preparation of the crystalline modification II of pyraclostrobin can be achieved by a process which comprises the following steps:
i) dissolving amorphous pyraclostrobin in an organic solvent comprising at least 50% by volume of at least one $C_1$-$C_4$-alkanol and preferably not more than 30% by volume, in particular not more than 10% by volume, of water; and
ii) effecting crystallization of pyraclostrobin over a period of less than 10 h in the absence of seed crystals of modification IV.

With respect to the dissolution of the pyraclostrobin, in particular the solvents, the temperatures, concentrations, etc., to be used, what was said for process IVa applies in an analogous manner.

Crystallization can, in principle, be effected analogously to the methods illustrated for process IVa. Typically, crystallization will be effected by cooling the solution by at least 20 K, in particular by 30 to 60 K.

In contrast to processes IVa and IVb, the total duration of the crystallization process, i.e. the period of time between the beginning of the measure which effects crystallization and the isolation of the pyraclostrobin by removal from the mother liquor is less than 10 h, in particular from 2 h to 8 h.

If appropriate, the crystallization will be carried out in the presence of seed crystals of modification II. In this case, the amount of seed crystals is typically from 0.01 to 10% by weight, frequently from 0.02 to 5% by weight, in particular from 0.03 to 1% by weight and especially from 0.05 to 0.5% by weight, based on the dissolved pyraclostrobin. The seed crystals are typically added during the crystallization of modification II and in particular at the beginning of the crystallization of modification II and preferably at or below the temperature at which the saturation concentration of pyraclostrobin in the solvent in question is reached.

In this manner, it is possible to prepare modification II having a pyraclostrobin content of at least 98% by weight, in particular at least 99% by weight. The proportion of modification II in the crystalline pyraclostrobin prepared in this manner is generally at least 90%.

In an X-ray powder diffractogram at 25° C., the crystalline modification III of pyraclostrobin shows at least three, in particular at least four, frequently at least five and especially all of the following reflexes:

$d=5.36\pm0.01$ Å

$d=5.39\pm0.01$ Å

$d=4.31\pm0.01$ Å

$d=3.68\pm0.01$ Å

$d=3.29\pm0.01$ Å

$d=2.82\pm0.01$ Å.

Crystalline pyraclostrobin of modification III typically has a melting point in the range from 59 to 60° C. The heat of fusion, i.e. the amount of energy required for melting the crystalline modification I, is about 69 to 72 J/g and in particular about 71±1 J/g.

Similarly to the preparation of modification I, preparation of modification III is achieved by crystallizing a pyraclostrobin melt, where, in contrast to the preparation of modification I, the melt is kept for a relatively long period of time at temperatures in the range from 18 to 25° C. (ambient temperature), until formation of the modification can be detected in the XRD. The modification can be stored at low temperatures, preferably below −15° C., for example in the range from −18 to −30° C., for a relatively long period of time.

As already mentioned above, modifications II and IV and in particular modification IV are/is suitable for preparing crop protection compositions and in particular for preparing aqueous suspension concentrates. Accordingly, the invention also provides a composition for crop protection, comprising pyraclostrobin in the form of modification IV or in the form of modification II, if appropriate a liquid phase and also, if appropriate, customary, generally solid carriers and/or auxiliaries.

Suitable carriers are, in principle, all solid substances usually used in crop protection compositions, in particular in fungicides. Solid carriers are, for example, mineral earths, such as silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

In the case of liquid formulations of the modifications II and/or IV, the compositions have a liquid phase. Suitable liquid phases are, in principle, water and also organic solvents in which pyraclostrobin has low or no solubility, for example those in which the solubility of pyraclostrobin at 25° C. and 1013 mbar is not more than 1% by weight, in particular not more than 0.1% by weight and especially not more than 0.01% by weight.

Typical auxiliaries comprise surfactants, in particular the wetting agents and dispersants usually employed in crop protection compositions, furthermore viscosity-modifying additives (thickeners), antifoam agents, antifreeze agents, agents for adjusting the pH, stabilizers, anticaking agents and biocides (preservatives).

The invention relates in particular to compositions for crop protection in the form of an aqueous suspension concentrate (SC). Such suspension concentrates comprise the pyraclostrobin of modification II and/or IV in a finely divided particulate form, where the pyraclostrobin particles are suspended in an aqueous medium. The size of the active compound particles, i.e. the size which is not exceeded by 90% by weight of the active compound particles, is typically below 30 µm, in particular below 20 µm. Advantageously, at least 40% by weight and in particular at least 60% by weight of the particles in the SCs according to the invention have diameters below 2 µm.

In addition to the active compound, suspension concentrates typically comprise surfactants, and also, if appropriate, antifoam agents, thickeners, antifreeze agents, stabilizers (biocides), agents for adjusting the pH and anticaking agents.

In such SCs, the amount of active compound, i.e. the total amount of pyraclostrobin of modification II and/or IV and, if appropriate, further active compounds is usually in the range from 10 to 70% by weight, in particular in the range from 20 to 50% by weight, based on the total weight of the suspension concentrate.

Preferred surfactants are anionic and nonionic surfactants. Suitable surfactants also include protective colloids. The amount of surfactants will generally be from 0.5 to 20% by weight, in particular from 1 to 15% by weight and particularly preferably from 1 to 10% by weight, based on the total weight of the SCs according to the invention. Preferably, the surfactants comprise at least one anionic surfactant and at least one nonionic surfactant, the ratio of anionic to nonionic surfactant typically being in the range from 10:1 to 1:10.

Examples of anionic surface-active substances (surfactants) include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and also polycarboxylates, such as, for example, polyacrylates, maleic anhydride/olefin copolymers (for example Sokalan® CP9, BASF), including the alkali metal, alkaline earth metal, ammonium and amine salts of the substances mentioned above. Preferred anionic surfactants are those which carry at least one sulfonate group, and in particular their alkali metal and their ammonium salts.

Examples of nonionic surfactants comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

Typical protective colloids are water-soluble amphiphilic polymers. Examples of these are proteins and denatured proteins, such as casein, polysaccharides, such as water-soluble starch derivatives and cellulose derivatives, in particular hydrophobically modified starches and celluloses, furthermore polycarboxylates, such as polyacrylic acid and acrylic acid copolymers, polyvinyl alcohol, polyvinylpyrrolidone, vinylpyrrolidone copolymers, polyvinylamines, polyethyleneimines and polyalkylene ethers.

In particular, the SCs according to the invention comprise at least one surfactant which improves wetting of the plant parts by the aqueous application form (wetting agent) and at least one surfactant which stabilizes the dispersion of the active compound particles in the SC (dispersant). The amount of wetting agent is typically in the range from 0.5 to 10% by weight, in particular from 0.5 to 5% by weight and especially from 0.5 to 3% by weight, based on the total weight of the SC. The amount of dispersant is typically from 0.5 to 10% by weight and in particular from 0.5 to 5% by weight, based on the total weight of the SC.

Preferred wetting agents are of anionic or nonionic nature and selected, for example, from naphthalenesulfonic acids including their alkali metal, alkaline earth metal, ammonium and amine salts, furthermore fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or nonionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers (for example Sokalan® CP9, BASF), including the alkali metal, alkaline earth metal, ammonium and amine salts of the substances mentioned above.

Viscosity-modifying additives (thickeners) suitable for the SCs according to the invention are in particular compounds which bestow upon the formulation pseudoplastic flow properties, i.e. high viscosity in the resting state and low viscosity in the agitated state. Suitable are, in principle, all compounds used for this purpose in suspension concentrates. Mention may be made, for example, of inorganic substances, such as bentonites or attapulgites (for example Attaclay® from Engelhardt), and organic substances, such as polysaccharides and heteropolysaccharides, such as Xanthan Gum® (Kelzan® from Kelco), Rhodopol® 23 (Rhone Poulenc) or Veegum® (from R.T. Vanderbilt), and preference is given to using Xanthan-Gum®. Frequently, the amount of viscosity-modifying additives is from 0.1 to 5% by weight, based on the total weight of the SC.

Antifoam agents suitable for the SCs according to the invention are, for example, silicone emulsions known for this purpose (Silikon® SRE, from Wacker, or Rhodorsil® from Rhodia), long-chain alcohols, fatty acids, defoamers of the type of aqueous wax dispersions, solid defoamers (so-called Compounds), organofluorine compounds and mixtures thereof. The amount of antifoam agent is typically from 0.1 to 1% by weight, based on the total weight of the SC.

Preservatives may also be added for stabilizing the suspension concentrates according to the invention. Suitable preservatives are those based on isothiazolones, for example Proxel® from ICI or Acticide® RS from Thor Chemie or Kathon® MK from Rohm & Haas. The amount of preservatives is typically from 0.05 to 0.5% by weight, based on the total weight of the SC.

Suitable antifreeze agents are liquid polyols, for example ethylene glycol, propylene glycol or glycerol. The amount of antifreeze agents is generally from 1 to 20% by weight, in particular from 5 to 10% by weight, based on the total weight of the suspension concentrate.

If appropriate, the SCs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

If the formulations of the crystalline modifications of the pyraclostrobin are used for treating seed, they may comprise further customary components used for treating seed, for example for dressing or coating. These include, in addition to the components mentioned above, in particular colorants, adhesives, fillers and plasticizers.

Suitable colorants are all dyes and pigments customary for such purposes. Both sparingly water-soluble pigments and water-soluble dyes can be used. Examples which may be mentioned are the dyes and pigments known under the names Rhodamine B, C.I. Pigment Red 112 and C.I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorant is usually not more than 20% by weight of the formulation and preferably in the range of from 0.1 to 15% by weight, based on the total weight of the formulation.

Suitable tackifiers are all binders customarily used in seed dressings. Examples of suitable binders include thermoplastic polymers, such as polyvinylpyrrolidone, polyvinyl acetate, polyvinyl alcohol and tylose, furthermore polyacrylates, polymethacrylates, polybutenes, polyisobutenes, polystyrene, polyethyleneamine, polyethyleneamide, the protective colloids mentioned above, polyesters, polyether esters, polyanhydrides, polyester urethanes, polyester amides, thermoplastic polysaccharides, for example cellulose derivatives, such as cellulose esters, cellulose ethers, cellulose ether esters, including methylcellulose, ethylcellulose, hydroxymethylcellulose, carboxymethylcellulose, hydroxypropylcellulose and starch derivatives and modified starches, dextrins, maltodextrins, alginates and chitosans, furthermore fats, oils, proteins, including casein, gelatine and zein, gum Arabic, shellac. The tackifiers are preferably compatible with plants, i.e. they have no significant, if any, phytotoxic action. The tackifiers are preferably biodegradable. Preferably, the tackifier is chosen such that it acts as a matrix for the active components of the formulation. The amount of tackifier is usually not more than 40% by weight of the formulation and preferably in the range of from 1 to 40% by weight and in particular in the range of from 5 to 30% by weight, based on the total weight of the formulation.

In addition to the tackifier, the formulation may also comprise inert fillers. Examples of these are the solid carrier materials mentioned above, in particular finely divided inorganic materials, such as clays, chalk, bentonite, kaolin, talc, perlite, mica, silica gel, diatomaceous earth, quartz powder, montmorillonite, and also finely divided organic materials, such as wood meal, cereal meal, activated carbon and the like. The amount of filler is preferably chosen such that the total amount of filler does not exceed 75% by weight, based on the total weight of all non-volatile components of the formulation. Frequently, the amount of filler is in the range of from 1 to 50% by weight, based on the total weight of all non-volatile components of the formulation.

In addition, the formulation may also comprise a plasticizer which increases the flexibility of the coating. Examples of plasticizers are oligomeric polyalkylene glycols, glycerol, dialkyl phthalates, alkyl benzyl phthalates, glycol benzoates and similar compounds. The amount of plasticizer in the coating is frequently in the range of from 0.1 to 20% by weight, based on the total weight of all non-volatile components of the formulation.

Pyraclostrobin in the form of modification IV or in the form of modification II can be used in a manner known per se for controlling phytopathogenic fungi. In particular, it can be formulated together with further active compounds, to increase the activity and/or to widen the activity spectrum. These include, in principle, all insecticides and fungicides which are typically used together with pyraclostrobin. In crop protection, the novel modifications of pyraclostrobin can be used as foliar fungicides, as fungicides for seed dressing and as soil fungicides.

They are of particular importance for controlling a large number of fungi on various crop plants, such as wheat, rye, barley, triticale, oats, rice, corn, grass, bananas, cotton, soybeans, coffee, sugarcane, grapevines, fruit and ornamental plants and vegetable plants, such as cucumbers, beans, tomatoes, potatoes and cucurbits, and also on the seeds of these plants.

Modifications II and IV are particularly suitable for the joint formulation as suspension concentrates with active compounds which for their part can be formulated as suspension concentrates. Accordingly, a preferred embodiment of the invention relates to suspension concentrates which, in addition to pyraclostrobin of modification II and/or modification IV, comprise at least one further active compound in finely divided, particulate form. With respect to particle sizes, amount of active compound and auxiliaries, what was said above applies.

Typical mixing partners of pyraclostrobin are, for example:
- acylalanines, such as benalaxyl, metalaxyl, ofurace, oxadixyl,
- amine derivatives such as aldimorph, dodine, dodemorph, fenpropimorph, fenpropidin, guazatine, iminoctadine, spiroxamine, tridemorph,
- anilinopyrimidines, such as pyrimethanil, mepanipyrim or cyprodinyl,
- antibiotics, such as cycloheximide, griseofulvin, kasugamycin, natamycin, polyoxin or streptomycin,
- azoles, such as bitertanol, bromoconazole, cyproconazole, difenoconazole, diniconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole,
- dicarboximides, such as iprodione, myclozolin, procymidone, vinclozolin,
- dithiocarbamates, such as ferbam, nabam, maneb, mancozeb, metam, metiram, propineb, polycarbamate, thiram, ziram, zineb,
- heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, thiophanate-ethyl, tiadinil, tricyclazole, triforine,
- nitrophenyl derivatives, such as binapacryl, dinocap, dinobuton, nitrophthal-isopropyl,
- phenylpyrroles, such as fenpiclonil or fludioxonil,
- sulfur,
- other fungicides, such as acibenzolar-S-methyl, benthiavalicarb, carpropamid, chlorothalonil, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, toloclofos-methyl, quintozene, zoxamide,
- sulfenic acid derivatives, such as captafol, captan, dichlofluanid, folpet, tolylfluanid,
- cinnamides and analogs, such as dimethomorph, flumetover or flumorph,
- 6-aryl[1,2,4]triazolo[1,5-a]pyrimidines as described, for example, in WO 98/46608, WO 99/41255 or WO 03/004465, in each case by the formula I,
- amide fungicides, such as cyflufenamid, and also (Z)-N-[α-(cyclopropylmethoxyimino)-2,3-difluoro-6-(difluoromethoxy)benzyl]-2-phenylacetamide.

Preferred mixing partners of pyraclostrobin are: metalaxyl, dodemorph, fenpropimorph, fenpropidin, guazatine, spiroxamine, tridemorph, pyrimethanil, cyprodinyl, bitertanol, bromoconazole, cyproconazole, difenoconazole, dinitroconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole, iprodione, vinclozolin, maneb, mancozeb, metiram, thiram, boscalid, carbendazim, carboxin, oxycarboxin, cyazofamid, dithianon, famoxadone, fenamidone, fenarimol, flutolanil, quinoxyfen, thiophanate-methyl, thiophanate-ethyl, triforine, dinocap, nitrophthal-isopropyl, phenylpyrroles, such as fenpiclonil or fludioxonil, acibenzolar-S-methyl, benthiavalicarb, carpropamid, chlorothalonil, cyflufenamid, cymoxanil, fenhexamid, fentinacetate, fenoxanil, fluazinam, fosetyl, fosetyl-aluminum, iprovalicarb, metrafenone, zoxamide, captan, folpet, dimethomorph, azoxystrobin, dimoxystrobin, fluoxastrobin, kresoxim-methyl, metominostrobin, orysastrobin, picoxystrobin or trifloxystrobin.

Particularly preferred mixing partners are metalaxyl, fenpropimorph, fenpropidin, guazatine, spiroxamine, pyrimethanil, cyprodinyl, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, iprodione, vinclozolin, boscalid, carbendazim, carboxin, oxycarboxin, cyazofamid, dithianon, quinoxyfen, thiophanate-methyl, thiophanate-ethyl, dinocap, nitrophthal-isopropyl, fenpicionil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxastrobin, kresoxim-methyl, metominostrobin, orysastrobin, picoxystrobin or trifloxystrobin.

Very particularly preferred mixing partners are fenpropimorph, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, boscalid, dithianon, quinoxyfen, thiophanate-methyl, thiophanate-ethyl, dinocap, fenpiclonil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxastrobin, kresoxim-methyl, metominostrobin, orysastrobin, picoxystrobin or trifloxystrobin.

Using the formulations according to the invention of the crystalline modifications of pyraclostrobin, it is, in principle, possible to control all harmful fungi which can also be controlled using the known formulations of pyraclostrobin. Depending on the respective mixing partner, these are, for example, the following plant diseases:

*Alternaria* species on vegetables, oilseed rape, sugarbeets, soybeans, cereals, cotton, fruit and rice (for example *A. solani* or *A. alternata* on potatoes and other plants),

*Aphanomyces* species on sugarbeet and vegetables,

*Ascochyta* sp. on cotton and rice,

*Bipolaris* and *Drechslera* species on corn, cereals, rice and lawn (for example *D. teres* on barley, *D. tritci-repentis* on wheat),

*Blumeria graminis* (powdery mildew) on cereals,

*Botrytis cinerea* (gray mold) on strawberries, vegetables, flowers and grapevines,

*Botryodiplodia* sp. on cotton,

*Bremia lactucae* on lettuce,

*Cercospora* species on corn, soybeans, rice and sugarbeet (for example *C. beticula* on sugarbeet),

*Cochliobolus* species on corn, cereals, rice (for example *Cochliobolus sativus* on cereals, *Cochliobolus miyabeanus* on rice),

*Corynespora* sp. on soybeans, cotton and other plants,

*Colletotrichum* species on soybeans, cotton and other plants (for example *C. acutatum* on various plants),

*Curvularia* sp. on cereals and rice,

*Diplodia* sp. on cereals and rice,

*Exserohilum* species on corn,

*Erysiphe cichoracearum* and *Sphaerotheca fuliginea* on cucumber plants,

*Fusarium* and *Verticillium* species (for example *V. dahliae*) on various plants (for example *F. graminearum* on wheat),
*Gaeumanomyces graminis* on cereals,
*Gibberella* species on cereals and rice (for example *Gibberella fujikuroi* on rice),
Grainstaining complex on rice,
*Helminthosporium* species (for example *H. graminicola*) on corn and rice,
*Macrophomina* sp. on soybeans and cotton,
*Michrodochium* sp. for example *M. nivale* on cereals,
*Mycosphaerella* species on cereals, bananas and peanuts (*M. graminicola* on wheat, *M. fijiesis* on bananas),
*Phaeoisaripsis* sp. on soybeans,
*Phakopsara* sp. for example *P. pachyrhizi* and *Phakopsara meibomiae* on soybeans,
*Phoma* sp. on soybeans,
*Phomopsis* species on soybeans, sunflowers and grapevines (*P. viticola* on grapevines, *P. helianthii* on sunflowers),
*Phytophthora infestans* on potatoes and tomatoes,
*Plasmopara viticola* on grapevines,
*Penecilium* sp. on soybeans and cotton,
*Podosphaera leucotricha* on apples,
*Pseudocercosporella herpotrichoides* on cereals,
*Pseudoperonospora* species on hops and cucumber plants (for example *P. cubenis* on cucumber),
*Puccinia* species on cereals, corn and asparagus (*P. triticina* and *P. striformis* on wheat, *P. asparagi* on asparagus),
*Pyrenophora* species on cereals,
*Pyricularia oryzae, Corticium sasakii, Sarocladium oryzae, S. attenuatum, Entyloma oryzae* on rice,
*Pyricularia grisea* on lawn and cereals,
*Pythium* spp. on lawn, rice, corn, cotton, oilseed rape, sunflowers, sugarbeet, vegetables and other plants,
*Rhizoctonia*-species (for example *R. solani*) on cotton, rice, potatoes, lawn, corn, oilseed rape, potatoes, sugarbeet, vegetables and other plants,
*Rynchosporium* sp. (for example *R. secalis*) on rice and cereals,
*Sclerotinia* species (for example *S. sclerotiorum*) on oilseed rape, sunflowers and other plants,
*Septoria tritici* and *Stagonospora nodorum* on wheat,
*Erysiphe* (syn. *Uncinula necator*) on grapevines,
*Setospaeria* species on corn and lawn,
*Sphacelotheca reilinia* on corn,
*Thievaliopsis* species on soybeans and cotton,
*Tilletia* species on cereals,
*Ustilago* species on cereals, corn and sugarbeet and
*Venturia* species (scab) on apples and pears (for example *V. inaequalis* on apple).

In a manner known per se, the modifications II and IV according to the invention of pyraclostrobin can also be formulated with insecticidally, acaricidally or nematicidally active compounds. It has been found to be particularly advantageous to use modifications II and IV of pyraclostrobin together with at least one active compound which is active against stinging, chewing, biting or sucking insects and other arthropods, for example from the order of the Coleoptera, in particular *Phyllophaga* sp., such as *Phyllophaga cuyabana*, *Sternechus* sp., such as *Sternechus pingusi*, *Sternechuns subsignatus*, *Promecops* sp. such as *Promecops carinicollis*, *Aracanthus* sp. such as *Aracanthus morei*, and *Diabrotica* sp. such as *Diabrotica speciosa, Diabrotica longicornis, Diabrotica 12-punctata, Diabrotica virgifera, Oryzophagus* sp., Lepidoptera, in particular *Elasmopalpus* sp. such as *Elasmopalpus* sp. such as *Elasmopalpus lignosellus, Diloboderus* sp.
Isoptera, in particular *Rhinotermitida*,
Homoptera, in particular *Dalbulus maidis*, or against nematodes, including root-knot nematodes, for example *Meloidogyne* spp., such as *Meloidogyne hapla, Meloidogyne incognita, Meloidogyne javanica*, and other *Meloidogyne* species; cyste-forming nematodes, such as *Globodera rostochiensis* and other *Globodera* species; *Heterodera avenae, Heterodera glycines, Heterodera schachtii, Heterodera trifolii*, and other *Heterodera* species; gall nematodes, for example *Anguina* species; stem eelworms and foliar nematodes, such as *Aphelenchoides* species.

A formulation comprising a modification II and/or IV according to the invention of pyraclostrobin and thiophanate-methyl or thiophanate-ethyl, for example, can be used for controlling the following harmful fungi:

*Alternaria* sp. on cereals, cotton and rice
*Ascochyta* sp. on cotton and rice,
*Botryodiplodia* sp. on cotton,
*Cercospora* species on corn, soybeans, rice and other plants,
*Corynespora* sp. on soybeans, cotton and other plants,
*Colletotrichum* species on soybeans, cotton and other plants,
*Curvularia* sp. on cereals and rice,
*Diplodia* sp. on cereals and rice,
*Drechslera* sp. on cereals and rice,
*Fusarium* sp. on cereals, soybeans and cotton,
*Giberella* sp. on cereals and rice,
*Macrophomia* sp. on soybeans and cotton,
*Penecilium* sp. on soybeans and cotton,
*Phaeoisaripsis* sp. on soybeans,
*Phoma* sp. on soybeans,
*Phomopsis* sp. on soybeans,
*Pythium* sp. on soybeans and cotton,
*Pyrenophora* sp.,
*Pyricularia* sp. on rice,
*Rhizoctonia* sp. on soybeans, rice and cotton,
*Rhychosporium* sp. on rice,
*Septoria* sp. on soybeans,
*Tilletia* sp. on cereals and rice,
*Ustilago* sp. on cereals.

A formulation comprising a modification II and/or IV according to the invention of pyraclostrobin, thiophanate-methyl or thiophanate-ethyl and fipronil or another GABA antagonist, such as acetoprole, endosulfan, ethiprole, vaniliprole, pyrafluprole or pyriprole, for example, can be used for controlling the harmful fungi mentioned above with simultaneous control of insects, for example Coleoptera, in particular *Phyllophaga* sp., such as *Phyllophaga cuyabana*, *Sternechus* sp., such as *Sternechus pingusi, Sternechuns subsignatus, Promecops* sp., such as *Promecops carinicollis, Aracanthus* sp., such as *Aracanthus morei*, and *Diabrotica* sp., such as *Diabrotica speciosa, Diabrotica longicornis, Diabrotica 12-punctata, Diabrotica virgifera, Oryzophagus* sp., and
Lepidoptera, in particular *Elasmopalpus* sp., such as *Elasmopalpus lignosellus, Diloboderus* sp.

A formulation comprising a modification II and/or IV according to the invention of pyraclostrobin and epoxyconazole, for example, can be used for controlling the following harmful fungi:

*Microdochium* sp. on cereals.
*Tilletia* sp. on cereals and rice,
*Ustilago* sp. on cereals.

A formulation comprising a modification II and/or IV according to the invention of pyraclostrobin, triticonazole and prochloraz or prochloraz-CuCl, for example, can be used for controlling the following harmful fungi:

*Microdochium* sp. on cereals,
*Tilletia* sp. on cereals and rice,
*Ustilago* sp. on cereals.

The novel modifications II and IV of pyraclostrobin allow the preparation of low-solvent or solvent-free aqueous suspension concentrates both of pyraclostrobin on its own and of pyraclostrobin with other crop protection agents, in particular the mixing partners indicated above. The solvent content, in particular the content of aromatic hydrocarbons, minus any antifreeze agents, is generally not more than 2% by weight of the suspension concentrate and is frequently below 2% by weight. The suspension concentrates according to the invention are distinguished in particular by better storage stability compared to the known pyraclostrobin-comprising suspension concentrates and suspoemulsion concentrates.

The figures and examples below serve to illustrate the invention and are not to be understood as limiting it.

ANALYSIS

The pictures of the X-ray powder diffractograms were taken using a D-5000 diffractometer from Siemens in reflection geometry in the range from 2θ=4°–35° with increments of 0.02° using Cu—Kα radiation at 25° C. The 2θ values found were used to calculate the stated interplanar spacing d.

The crystallographic data of modifications II and IV (Tables 1 and 2) were determined on a single-crystal diffractometer from Siemens using Cu—Kα radiation.

Melting points and heats of fusion were determined by DSC using a Simultaneous Thermal Analyzer STA 449 C Jupiter from NETZSCH with a heating rate of 5 K/min in the range from −5° to +80° C. The amount of sample was 5 to 10 mg.

The particle sizes in the suspension concentrates were determined using a Mastersizer 2000 from Malvern Instruments GmbH.

PREPARATION EXAMPLES

Example 1

Figure 1:
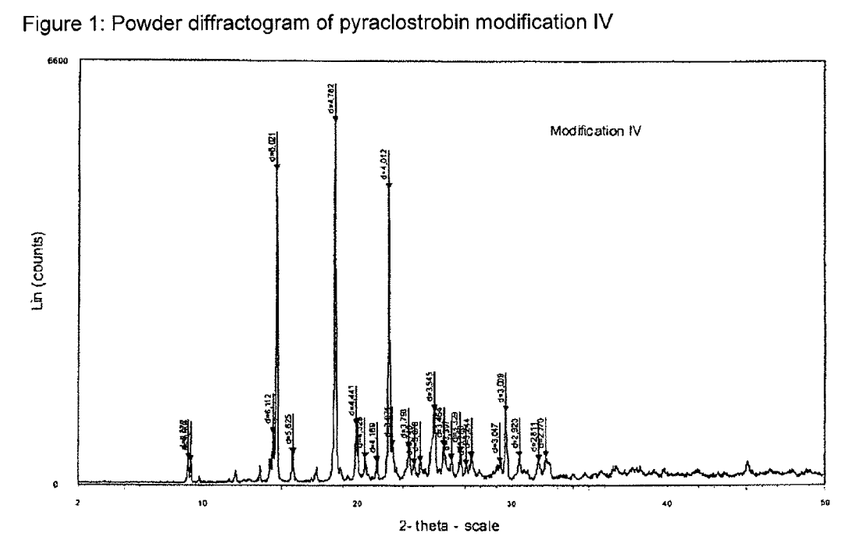
FIG. 1: X-ray powder diffractogram of modification IV

Preparation of Pyraclostrobin Modification IV by Crystallization from Isopropanol Using Seed Crystals of Modification IV Practice 600 g of isopropanol are heated to 70° C. Separately, 300 g of amorphous pyraclostrobin are converted at 80° C. into a melt of low viscosity. With vigorous stirring, this melt is added to the isopropanol. The mixture is kept at 70° C. until the material is fully dissolved (about 30 minutes). Subsequently, the mixture is allowed to cool to room temperature. With stirring, 1 g of crystalline pyraclostrobin of modification IV is added. After about 1 hour, crystallization sets in. The mixture is stirred for a further 18 hours and the crystals are filtered off and dried under reduced pressure at 25° C. Yield: 290 g of pyraclostrobin. Modification IV was identified by its reflexes in the X-ray powder diffractogram (FIG. 1).

Example 2

Preparation of Pyraclostrobin Modification IV by Crystallization from Ethanol Using Seed Crystals of Modification IV In a 2.5 l vessel with double mantle and turbine stirrer (PBT turbine), 1500 g of ethanol are initially charged and heated to 50° C. 1000 g of pyraclostrobin are heated to 70° C. and added to the reaction vessel. After 10 min of stirring at 60° C., the resulting clear solution is allowed to cool slowly. At 34° C., 1 g of seed crystals of modification IV is added. Over a period of 114-116 hours, the mixture is then allowed to cool to ambient temperature. The mixture is then cooled to 10° C. The solid is isolated, washed with 400 ml of cold ethanol and, under reduced pressure (40 mbar) and at ambient temperature, dried for a period of about 16 hours. Yield: 870 g (melting point 67° C.). Modification IV was identified by its reflexes in the X-ray powder diffractogram (see FIG. 1).

Example 3

Preparation of Pyraclostrobin Modification IV by Crystallization from Isopropanol Without Seed Crystals 100 g of isopropanol are heated to 60° C. 15 g of pyraclostrobin are then added and the mixture is stirred until all the material has dissolved. The mixture is then allowed to cool to ambient temperature and stirred for another 2 weeks. The crystals are filtered off and dried under reduced pressure and at ambient temperature for 16 h. Yield: 12 g.

In an X-ray powder diffractometry, the material obtained showed the diagram shown in FIG. 1.

Example 4

Figure 2:
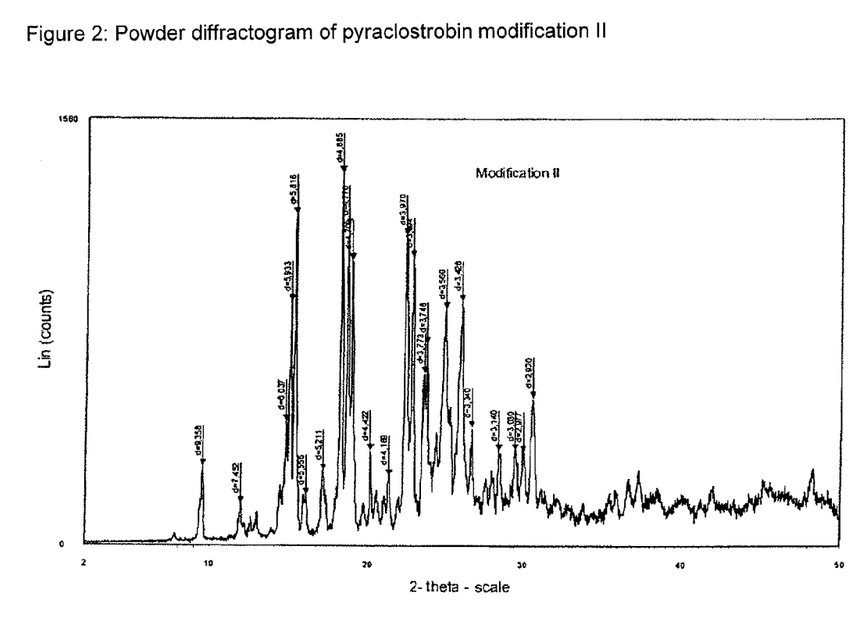
FIG. 2: X-ray powder diffractogram of modification II

Preparation of Pyraclostrobin Modification II by Crystallization from Isopropanol Without Seed Crystals 100 g of isopropanol are heated to 60° C. With stirring, 15 g of pyraclostrobin are then added, and the mixture is stirred until all the material has dissolved. The mixture is then allowed to cool to 20° C. and stirred for another 4 hours. The mixture is then cooled to 10° C. and stirred for a further hour. The crystals are isolated immediately and dried under reduced pressure and at ambient temperature for 16 h. Yield: 12 g. In an X-ray powder diffractometry, the material obtained showed the diagram shown in FIG. 2.

Example 5

Preparation of Pyraclostrobin Modification I by Crystallization from the Melt

Amorphous pyraclostrobin was melted and slowly cooled. Modification I crystallizes first from the pyraclostrobin melt.

Figure 3:
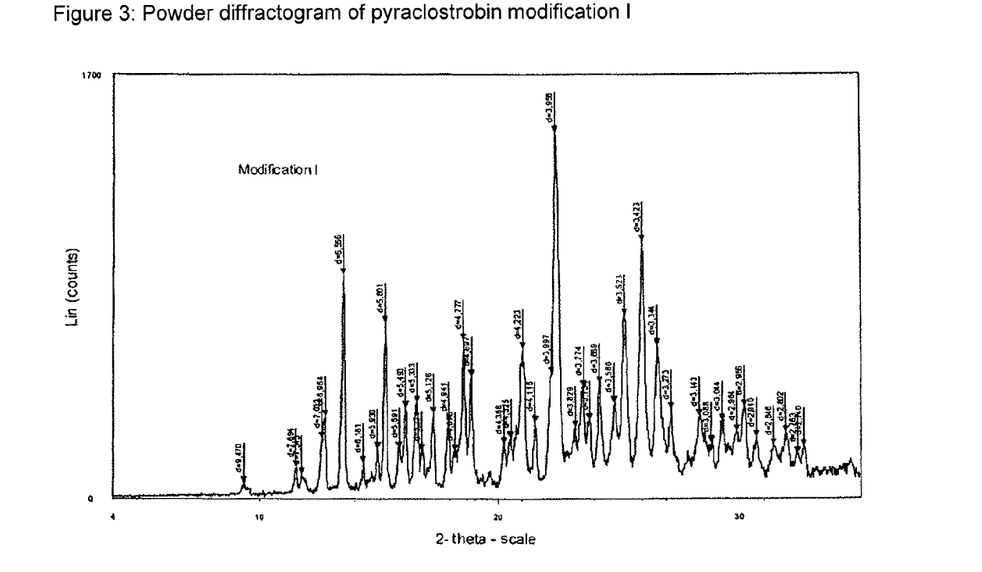
FIG. 3: X-ray powder diffractogram of modification I

The crystallization is accelerated by tempering at about 40° to 45° C. The material obtained has the X-ray powder diffractogram shown in FIG. 3.

Example 6

Preparation of Pyraclostrobin Modification III by Crystallization from the Melt

Figure 4:
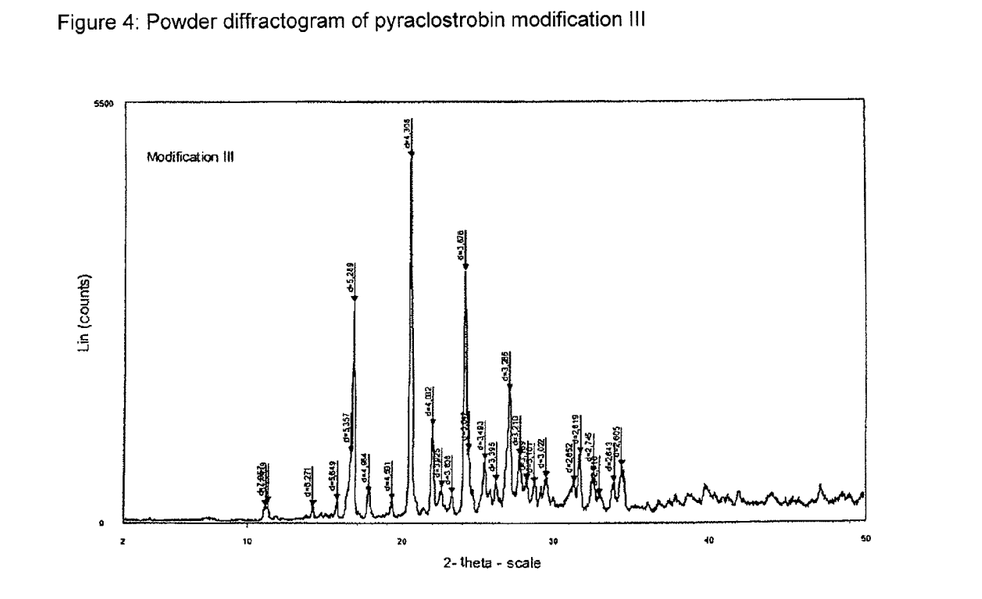
FIG. 4: X-ray powder diffractogram of modification III

This modification crystallizes after a number of weeks from a pyraclostrobin melt if the melt is kept at a temperature in the range from 18 to 25° C. In an X-ray powder diffractometry, the material obtained showed the diagram shown in FIG. 4.

Example 7

Preparation of Pyraclostrobin of Modification IV by Crystallization from Ethanol in the Presence of Seed Crystals 358 g of pyraclostrobin having a purity of 99% were liquefied at 80° C. and stirred with 525 g of ethanol (96%) until the pyraclostrobin was fully dissolved. Over a period of 5 h, the mixture was then cooled to 35° C., and about 1 g of seed crystals of modification IV was added at this temperature. Over a period of 3 h, the mixture was then cooled to 20° C., and 483 g of water were then added over a period of 2 h. After the addition of water had ended, stirring at 20° C. was continued for another hour and the mixture was then filtered using a notch (porosity 4). After washing with 350 g of water, the crystalline solid obtained was dried under reduced pressure at 40° C. This gave 353 g of a crystalline product which was identified as modification IV. Yield: 98.6%, content: 99.5%, melting point: 63.0° C.

Example 8

Preparation of Pyraclostrobin of Modification IV by Crystallization from Methanol in the Presence of Seed Crystals 179.4 g of active compound I were liquefied at 80° C. and stirred with 253 g of methanol (96%) until the pyraclostrobin was fully dissolved. Over a period of 4 h, the mixture was then cooled to 35° C., and about 0.5 g of seed crystals of modification IV was added at this temperature. Over a period of 2 h, the mixture was then cooled to 20° C., and 252 g of water were then added over a period of 1.5 h. After the addition of water had ended, stirring at 20° C. was continued for another hour and the mixture was then filtered using a notch (porosity 4). After washing with 90 g of water, the crystalline solid obtained was dried under reduced pressure at 40° C. This gave 177.8 g of a crystalline product which was identified as modification IV. Yield: 99.1%, content: 99.8%, melting point: 65.0° C.

Example 9

Preparation of Pyraclostrobin of Modification IV by Crystallization from Methanol in the Presence of Seed Crystals 179.4 g of active compound I were liquefied at 80° C. and stirred with 253 g of methanol (96%) until the pyraclostrobin was fully dissolved. Over a period of 3 h, the mixture was then cooled to 35° C., and about 0.5 g of seed crystals of modification IV was added at this temperature. Over a period of 2 h, the mixture was then cooled to 20° C., and 252 g of water were then added over a period of 1.5 h. After the addition of water had ended, stirring at 20° C. was continued for another hour and the mixture was then filtered using a notch (porosity 3). After washing with 90 g of water, the crystalline solid obtained was separated off. This gave 236.4 g of a water-moist crystalline product which had an active compound content of 75.3%. This corresponds to a yield of 99.2%. A sample of the product obtained was dried under reduced pressure at 40° C. This gave a crystalline product which was identified as modification IV and had a melting point of 65.2° C.

Comparative Example 1

Crystallization analogously to example 1 but using ethyl acetate instead of isopropanol gave a solidifying oil and poor yields of pyraclostrobin.

Comparative Example 2

Crystallization analogously to Example 1 but, in contrast to the method described therein, without the use of seed crystals gave a solidifying oil and poor yields of pyraclostrobin.

FORMULATION EXAMPLES

Comparative Formulation Example

Preparation of a Suspension Concentrate of Pyraclostrobin Adsorbed on Silicic Acid Pyraclostrobin Premix
Water (about 60% by weight of the total formulation) is initially charged in a suitable vessel. Wetting agent and then silicic acid are stirred in, and the mixture is heated to 80° C. 20 parts by weight of a pyraclostrobin melt, heated to 80° C., are then added with stirring, and after the end of the addition stirring at 80° C. is continued for a further 30 minutes. With stirring, the suspension is then cooled to ambient temperature. The premix had the following composition:

| | |
|---|---|
| Water | 60 parts by weight |
| Wetting agent | 5 parts by weight of (naphthalenesulfonic acid/formaldehyde condensate) |
| Silicic acid | 15 parts by weight (precipitated silicic acid) |
| Pyraclostrobin | 20 parts by weight |

Finished Formulation:
Water is initially charged in a suitable vessel. With stirring, wetting agent, dispersant, antifreeze agent, stabilizer and partial amounts of the defoamer are then added. The second active compound and the pyraclostrobin premix are added to this mixture. The dispersion is then ground in a bead mill with effective cooling to the desired fineness.

With addition of the remaining formulation auxiliaries (bactericide, thickener, remaining defoamer), the formulation is then finished. The finished formulation had the following composition:

| | |
|---|---|
| Water | 42.3 parts by weight |
| Wetting agent | 4 parts by weight (naphthalenesulfonic acid/formaldehyde condensate) |
| Silicic acid | 7.5 parts by weight (precipitated silicic acid) |

-continued

| | |
|---|---|
| Pyraclostrobin | 10 parts by weight |
| Dispersant | 3 parts by weight (EO/PO block copolymer) |
| Antifreeze agent | 2 parts by weight (propylene glycol) |
| Defoamer | 0.5 part by weight (commercial silicone defoamer, for example Silfoam types from Wacker) |
| Stabilizer | 0.2 part by weight (buffer system) |
| Active compound | 30 parts by weight (folpet) |
| Bactericide | 0.2 part by weight (substituted isothiazolin-3-ones) |
| Thickener | 0.3 part by weight (xanthan gum) |

Formulation Example 1

Preparation of a Suspension Concentrate of Pyraclostrobin in Modification IV The residual amount of water is initially charged in a suitable vessel. The further formulation components: wetting agent, dispersant, antifreeze agent, stabilizer and partial amounts of the defoamer are then stirred in. Crystalline pyraclostrobin and the second solid active compound are then added. The dispersion is then ground in a bead mill with effective cooling to the desired fineness. The formulation is then finished with addition of the remaining formulation auxiliaries.

| | |
|---|---|
| Water | 46.9 parts by weight |
| Wetting agent | 3 parts by weight (naphthalenesulfonic acid/formaldehyde condensate) |
| Pyraclostrobin | 10 parts by weight |
| Dispersant | 2 parts by weight (polyethylene oxide/polypropylene oxide block copolymer (EO/PO block copolymer)) |
| Antifreeze agent | 7 parts by weight (propylene glycol) |
| Defoamer | 0.5 part by weight (commercial silicone defoamer, for example Silfoam types from Wacker) |
| Stabilizer | 0.1 part by weight (buffer system) |
| Active compound | 30 parts by weight (folpet) |
| Bactericide | 0.2 part by weight (substituted isothiazolin-3-ones) |
| Thickener | 0.3 part by weight (xanthan gum) |

To determine the stability, the formulations were stored at 40° C. for the period stated in Table 3. To determine the particle size by light scattering, a sample was diluted and dispersed in water, and the particle size distribution was then determined using the Mastersizer 2000.

Figure 5:
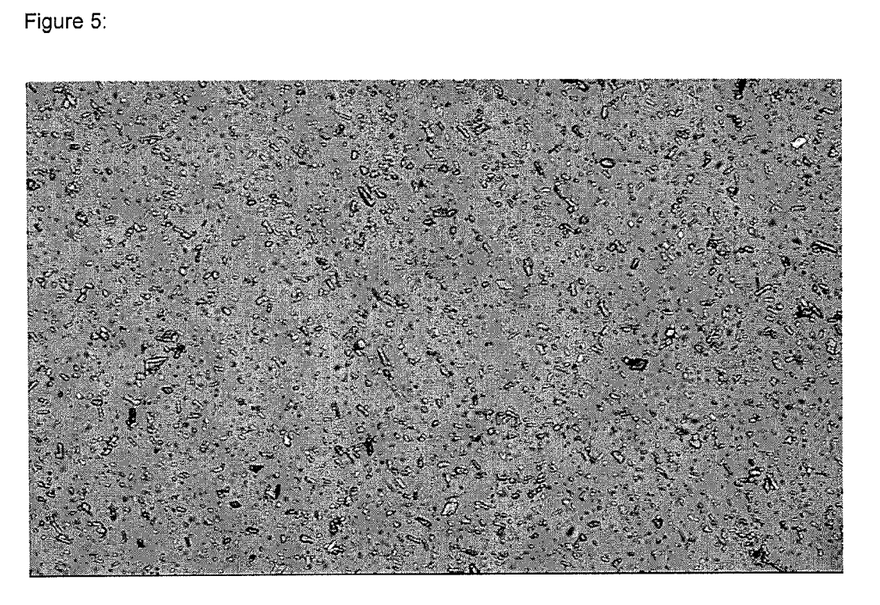
FIG. 5: Picture of the formulation from formulation example 1 taken with a light microscope after 26 weeks of storage at 40° C.
Figure 6:
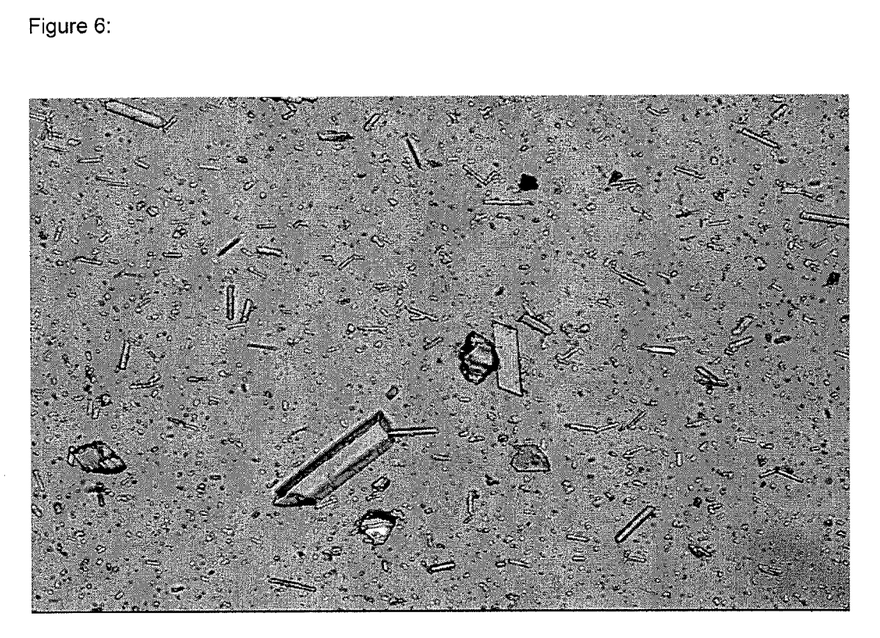
FIG. 6: Picture of the formulation of comparative formulation example taken with a light microscope after 26 weeks of storage at 40° C.

The light microscope pictures of a 5% strength dilution shown in FIGS. 5 and 6 were taken with a Leica microscope using a 3 CCD Color Vision Camera module.

To determine the stability of the dispersion, a 2% strength dilution was prepared in a 100 ml pointed cylinder. The volume of the sediment formed was read off after a standing time of 2 hours.

TABLE 3

| | Storage stability | |
|---|---|---|
| | Comparative example | Formulation example 1 |
| Stability of a 2% dispersion, 2 h | | |
| after 4 weeks of storage, 40° C. | 0.4 ml of sediment | 0.15 ml of sediment |
| after 26 weeks of storage, 40° C. | 0.5 ml of sediment | 0.3 ml of sediment |
| Particle size distribution after 4 weeks of storage, 40° C. | | |
| <2 μm[1] | 56% | 65% |
| 100%<[2] | 95 μm | 24 μm |
| after 26 weeks of storage, 40° C. | | |
| <2 μm | 42% | 57% |
| 100%< | 172 μm | 21 μm |

[1] % by weight of particles below 2 μm
[2] Maximum particle size

Analogously to Example 1, the following aqueous suspension concentrates were prepared:

Example 3

| | |
|---|---|
| Water | 42 parts by weight |
| Wetting agent | 2.6 parts by weight (naphthalenesulfonic acid/formaldehyde condensate) |
| Pyraclostrobin | 4 parts by weight |
| Dispersant | 2.7 parts by weight (EO/PO block copolymer) |
| Antifreeze agent | 6.3 parts by weight (propylene glycol) |
| Defoamer | 0.5 part by weight (commercial silicone defoamer, for example Silfoam types from Wacker) |
| Stabilizer | 1.4 parts by weight (buffer system) |
| Active compound | 40 parts by weight (folpet) |
| Bactericide | 0.2 part by weight (substituted isothiazolin-3-ones) |
| Thickener | 0.3 part by weight (xanthan gum) |

Example 4

| | |
|---|---|
| Water | 47 parts by weight |
| Wetting agent | 2 parts by weight (naphthalenesulfonic acid/formaldehyde condensate) |
| Pyraclostrobin | 40 parts by weight |
| Dispersant | 3 parts by weight (EO/PO block copolymer) |
| Antifreeze agent | 7 parts by weight (propylene glycol) |
| Defoamer | 0.5 part by weight (commercial silicone defoamer, for example Silfoam types from Wacker) |
| Bactericide | 0.2 part by weight (substituted isothiazolin-3-ones) |
| Thickener | 0.3 part by weight (xanthan gum) |

Example 5

| | |
|---|---|
| Water | 47.1 parts by weight |
| Wetting agent | 2 parts by weight (naphthalenesulfonic acid/formaldehyde condensate) |
| Pyraclostrobin | 10 parts by weight |
| Dispersant | 3 parts by weight (EO/PO block copolymer) |
| Antifreeze agent | 7 parts by weight (propylene glycol) |
| Defoamer | 0.5 part by weight (commercial silicone defoamer, for example Silfoam types from Wacker) |

-continued

| | |
|---|---|
| Active compound | 20 parts by weight (boscalid) |
| Bactericide | 0.2 part by weight (substituted isothiazolin-3-ones) |
| Thickener | 0.2 part by weight (xanthan gum) |

The results of the stability studies are compiled in Table 4.

TABLE 4

| | Storage stability | |
|---|---|---|
| | Example 3 | Example 5 |
| Stability of a 2% dispersion, 1 h | | |
| directly after preparation | trace of sediment | trace of sediment |
| after 4 weeks of storage, | | |
| 20° C. | trace of sediment | trace of sediment |
| 40° C. | 0.05 ml of sediment | trace of sediment |
| after 26 weeks of storage, | | |
| 20° C. | trace of sediment | trace of sediment |
| 40° C. | 0.05 ml of sediment | trace of sediment |
| Particle size distribution directly after preparation | | |
| <2 μm[1]/100%<[2] | 76%/11 μm | 72%/11 μm |
| after 4 weeks of storage at 20° C. | | |
| <2 μm[1]/100%<[2] at 40° C. | 68%/21 μm | 63%/15 μm |
| <2 μm[1]/100%<[2] after 26 weeks of storage, at 20° C. | 66%/21 μm | 40%/21 μm |
| <2 μm[1]/100%<[2] at 40° C. | 67%/24 μm | 56%/21 μm |
| <2 μm[1]/100%<[2] | 44%/33 μm | 33%/28 μm |

[1]% by weight of particles below 2 μm
[2]Maximum particle size

The invention claimed is:

1. A crystalline modification IV of pyraclostrobin which, in an X-ray powder diffractogram at 25° C., shows at least three of the following reflexes:

$d=6.02\pm0.01$ Å

$d=4.78\pm0.01$ Å

$d=4.01\pm0.01$ Å

$d=3.55\pm0.01$ Å

$d=3.01\pm0.01$ Å.

2. The crystalline modification IV according to claim 1 having a melting point in the range from 62 to 72° C.

3. The crystalline modification IV according to claim 1 having a pyraclostrobin content of at least 98% by weight.

4. A process for preparing a crystalline modification IV of pyraclostrobin according to any of the preceding claims, comprising:
   i) dissolving a pyraclostrobin form different from modification IV in an organic solvent or solvent mixture, where the organic solvent or solvent mixture comprises at least 70% by volume of at least one fully water-miscible organic solvent L1 and up to 30% by volume of water; and
   ii) effecting crystallization of pyraclostrobin over a period of at least 10 hours and/or in the presence of seed crystals of modification IV.

5. The process according to claim 4, where the pyraclostrobin is dissolved at a temperature above 50° C.

6. The process according to claim 5, wherein the solution is cooled to crystallize the pyraclostrobin.

7. The process according to claim 4, wherein the crystallization of the pyraclostrobin is effected by adding water to the pyraclostrobin solution.

8. The process according to claim 4, wherein seed crystals of modification IV are added during or prior to the crystallization of the pyraclostrobin.

9. The process according to claim 4, where the fully water-miscible organic solvent L1 is selected from $C_1$-$C_4$-alkanols, acetone and butanone.

10. The process according to claim 9, where, in step i), methanol, ethanol or a solvent mixture comprising at least 70% by volume of methanol and/or ethanol is used for dissolving the pyraclostrobin.

11. The process according to claim 4, wherein after a partial amount of the pyraclostrobin is crystallized in the solution, water is added to bring the crystallization of the pyraclostrobin to completion.

12. A process for preparing a crystalline modification IV of pyraclostrobin according to claim 1, comprising:
   i) preparing a suspension of a pyraclostrobin form different from modification IV in an organic solvent;
   ii) optionally, adding seed crystals of modification IV to the suspension;
   iii) agitating the suspension until at least 90% of the pyraclostrobin comprised therein is present in the form of modification IV.

13. The process according to claim 12, where the organic solvent used in step i) to suspend the pyraclostrobin comprises at least 50% by volume of at least one $C_1$-$C_4$-alkanol.

14. The process according to claim 13, where the organic solvent used in step i) to suspend the pyraclostrobin comprises at least 70% by volume of methanol, isopropanol and/or ethanol.

15. A composition for crop protection, comprising pyraclostrobin in the form of modification IV, carriers, and/or auxiliaries.

16. The composition according to claim 15 in the form of an aqueous suspension concentrate.

17. A method for controlling phytopathogenic fungi comprising contacting a plant, seed, or soil in need of treatment with a crystalline form of modification IV of pyraclostrobin.

* * * * *